(12) United States Patent
Kaneko et al.

(10) Patent No.: US 10,463,799 B2
(45) Date of Patent: Nov. 5, 2019

(54) MEDICAL SYRINGE, GASKET FOR USE IN THE SYRINGE, AND GASKET PRODUCTION METHOD

(71) Applicant: SUMITOMO RUBBER INDUSTRIES, LTD., Kobe-shi, Hyogo (JP)

(72) Inventors: Hiroyuki Kaneko, Kobe (JP); Hiroaki Nakano, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 85 days.

(21) Appl. No.: 15/191,613

(22) Filed: Jun. 24, 2016

(65) Prior Publication Data
US 2017/0021107 A1 Jan. 26, 2017

(30) Foreign Application Priority Data
Jul. 23, 2015 (JP) ................................. 2015-145697

(51) Int. Cl.
*A61M 5/315* (2006.01)
*B32B 25/08* (2006.01)
(Continued)

(52) U.S. Cl.
CPC ......... *A61M 5/31513* (2013.01); *B29C 35/02* (2013.01); *B29C 43/184* (2013.01);
(Continued)

(58) Field of Classification Search
CPC .. A61M 5/31513; B29D 99/0053; B32B 3/04; B32B 3/06; B32B 27/32;
(Continued)

(56) References Cited

U.S. PATENT DOCUMENTS 3,611,847 A * 10/1971 Derman ................... B26D 3/08
264/159
6,090,081 A 7/2000 Sudo et al.
(Continued)

FOREIGN PATENT DOCUMENTS

| EP | 2 781 231 A2 | 9/2014 |
| JP | 7-25953 Y2 | 6/1995 |

(Continued)

OTHER PUBLICATIONS

Extended European Search Report dated Nov. 28, 2016, in European Patent Application No. 16177101.9.

*Primary Examiner* — Lauren P Farrar
(74) *Attorney, Agent, or Firm* — Birch, Stewart, Kolasch & Birch, LLP

(57) ABSTRACT

A gasket (13) for use in a medical syringe is provided, which includes a main body (14) made of an elastic material, and a lamination film (15) provided on a surface of the main body (14). The gasket (13) has a circumferential surface portion (17) to be kept in contact with an inner peripheral surface of a syringe barrel (11) of the syringe. The gasket (13) has a groove (22) provided in the circumferential surface portion (17) thereof as extending circumferentially thereof. The groove (22) has a depth of not less than 0.8D (μm), preferably not less than D (μm), wherein D (μm) is the thickness of a portion of the lamination film (15) present in the circumferential surface portion (17) of the gasket (13).

6 Claims, 2 Drawing Sheets

(51) Int. Cl.
  *B29C 35/02*    (2006.01)
  *B29C 43/18*    (2006.01)
  *B29C 59/00*    (2006.01)
  *B29C 59/16*    (2006.01)
  *F16J 15/3284*  (2016.01)
  *B32B 7/12*     (2006.01)
  *B32B 27/08*    (2006.01)
  *B32B 27/32*    (2006.01)
  *B32B 3/04*     (2006.01)
  *B32B 3/06*     (2006.01)
  *B32B 3/26*     (2006.01)
  *B29D 99/00*    (2010.01)
  *B29K 23/00*    (2006.01)
  *B29K 627/18*   (2006.01)
  *B29L 31/26*    (2006.01)
  *B29L 31/00*    (2006.01)

(52) U.S. Cl.
  CPC .......... *B29C 59/007* (2013.01); *B29C 59/16* (2013.01); *B29D 99/0053* (2013.01); *B32B 3/04* (2013.01); *B32B 3/06* (2013.01); *B32B 3/26* (2013.01); *B32B 3/263* (2013.01); *B32B 7/12* (2013.01); *B32B 25/08* (2013.01); *B32B 27/08* (2013.01); *B32B 27/32* (2013.01); *B32B 27/322* (2013.01); *F16J 15/3284* (2013.01); *A61M 2207/00* (2013.01); *B29C 2043/189* (2013.01); *B29K 2023/22* (2013.01); *B29K 2627/18* (2013.01); *B29L 2031/265* (2013.01); *B29L 2031/7544* (2013.01); *B32B 2274/00* (2013.01); *B32B 2307/732* (2013.01); *B32B 2535/00* (2013.01); *B32B 2581/00* (2013.01)

(58) Field of Classification Search
  CPC .......... B32B 27/322; B32B 7/12; B32B 3/26; B32B 3/263; B32B 27/08; B32B 25/08; B32B 2307/732; F16J 15/3284; B29C 59/007; B29C 35/02; B29C 59/16; B29C 43/184
  See application file for complete search history.

(56) References Cited

U.S. PATENT DOCUMENTS

| | | | |
|---|---|---|---|
| 6,477,940 B1* | 11/2002 | Danckert | F02M 47/027 239/533.11 |
| 7,547,297 B2* | 6/2009 | Brinkhues | A61M 5/31513 604/187 |
| 2006/0178643 A1 | 8/2006 | Sudo et al. | |
| 2013/0040156 A1 | 2/2013 | Nakano et al. | |
| 2013/0053786 A1* | 2/2013 | Maeda | B29C 33/42 604/187 |
| 2014/0005630 A1* | 1/2014 | Bagaoisan | A61M 25/10182 604/500 |
| 2014/0339777 A1 | 11/2014 | Nakano et al. | |
| 2017/0296756 A1* | 10/2017 | Giraud | A61M 5/31578 |

FOREIGN PATENT DOCUMENTS

| | | |
|---|---|---|
| JP | 3282322 B2 | 5/2002 |
| JP | 3387775 B2 | 3/2003 |
| JP | 2003-190285 A | 7/2003 |
| JP | 2005-185747 A | 7/2005 |
| JP | 2006-181027 A | 7/2006 |
| JP | 4908617 B2 | 4/2012 |
| JP | 2014-46096 A | 3/2014 |
| JP | 2014-223149 A | 12/2014 |
| JP | 2015-146871 A | 8/2015 |

* cited by examiner

MEDICAL SYRINGE, GASKET FOR USE IN THE SYRINGE, AND GASKET PRODUCTION METHOD

TECHNICAL FIELD

The present invention relates to a medical syringe, particularly, to a gasket for use in the medical syringe, and a gasket production method.

BACKGROUND ART

Syringes prefilled with a liquid drug (prefilled syringes) are used as medical syringes. In recent years, the prefilled syringes are increasingly used, because the prefilled syringes can be easily handled without the need for transferring a liquid drug into the syringe and can prevent medical malpractice such as transfer of a wrong liquid drug into the syringe.

Unlike conventional syringes (into which a liquid drug sucked up from a vial or other container is transferred immediately before use), the prefilled syringes are required to serve as a container which is kept in contact with the liquid drug for a long period of time.

A gasket to be used for such a syringe is generally made of a crosslinked rubber. It is known that the crosslinked rubber typically contains various crosslinking components, and these crosslinking components and their thermally decomposed products are liable to migrate into the liquid drug when the liquid drug is kept in contact with the gasket. It is also known that these migrating components adversely influence the efficacy and the stability of some liquid drug.

When the syringe is used, the gasket is required to smoothly slide with respect to a barrel of the syringe. In general, the gasket made of the crosslinked rubber cannot be used because of its poorer slidability. Therefore, it is a general practice to apply a silicone oil onto a surface of the barrel or the gasket. However, it is known that the silicone oil adversely influences the efficacy and the stability of some liquid drug.

From this viewpoint, a so-called laminated gasket product is known, which includes a rubber gasket body having a surface laminated with a highly slidable film. By covering the surface of the rubber gasket body with the film, the components of the crosslinked rubber are prevented from migrating into the liquid drug. Further, sufficient slidability is ensured by laminating the surface with the highly slidable film without the silicone oil.

Exemplary materials for the film to be used for these purposes include ultrahigh molecular weight polyethylenes and fluororesins which are highly slidable. Of these materials, the fluororesins are preferred because of their high slidability and chemical stability. Of these fluororesins, polytetrafluoroethylenes (PTFE) are particularly preferred because of their very high slidability and stability.

CITATION LIST

Patent Document

Patent Document 1: JP-2005-185747-A

SUMMARY OF THE INVENTION

Problem to be Solved by the Invention

However, the film to be used for the aforementioned purposes does not have rubber elasticity and, therefore, impairs the rubber elasticity of the inside crosslinked rubber. The rubber elasticity of the gasket is essential for reliable sealing of the liquid drug contained in the syringe barrel. If the gasket has insufficient rubber elasticity, the gasket is liable to suffer from leakage of the liquid drug from the syringe barrel. Further, the gasket needs improvement in slidability when being inserted in the syringe barrel.

To cope with this, the inventors of the present invention further conducted studies to control the thickness of the film to be employed for the lamination and modify the surface of the film for improvement of the film.

In a general rubber product production process, a rubber is vulcanization-molded into a desired product shape in a mold having a cavity conformal to the desired product shape, and then the resulting product is demolded from the mold. In this production process, the product is rubbed against the mold when being demolded from the mold and, therefore, minute scratches are formed on the surface of the product. In a gasket production process, the gasket is taken out of the mold in a direction perpendicular to the circumference of the gasket. Scratches formed in the perpendicular direction on the surface of the gasket are unwanted, because the reliable liquid drug sealability is significantly impaired by the scratches.

In the molding of the laminated gasket, the surface of the gasket body is laminated with a less fluid film layer, so that the cavity of the mold is not perfectly filled. Therefore, the gasket product has insufficient shape followability with respect to the cavity of the mold. This makes it difficult, for example, to perfectly form a minute groove structure on the gasket product by the molding.

The inventors of the present invention conceived an idea that the aforementioned problem can be solved by molding a gasket laminated with a film and then forming a minute groove structure in a circumferential surface of the molded gasket, and attained the present invention.

Solution to Problem

According to inventive aspects, there is provided a laminated gasket for use in a medical syringe. According to other inventive aspects, there is provided a production method for a laminated gasket. According to another inventive aspect, there is provided a medical syringe.

These inventive aspects will be described more specifically.

According to the first inventive aspect, the gasket for use in the medical syringe includes a main body made of an elastic material and a lamination film provided on a surface of the main body, and the gasket has a circumferential surface portion to be kept in contact with an inner peripheral surface of a syringe barrel of the syringe. The gasket has a groove provided in the circumferential surface portion thereof as extending circumferentially thereof, and the groove has a depth of not less than 0.8D (μm) wherein D (μm) is the thickness of a portion of the lamination film present in the circumferential surface portion of the gasket.

According to the second inventive aspect, the depth of the groove is not less than D (μm) in the gasket of the first inventive aspect.

According to the third inventive aspect, the groove is a groove formed by laser processing in the gasket of the first inventive aspect.

According to the fourth inventive aspect, the gasket production method is a production method for producing the gasket of the first inventive aspect for use in the medical syringe, and includes the steps of: preparing a gasket molding mold; molding a gasket in the mold, the gasket having a surface laminated with a lamination film and including a circumferential surface portion; demolding the gasket from the mold, and then forming a groove extending circumferentially of the gasket in the circumferential surface portion of the gasket.

According to the fifth inventive aspect, the circumferential groove is formed in the circumferential surface portion of the gasket by laser irradiation in the groove forming step in the gasket production method of the fourth inventive aspect.

According to the sixth inventive aspect, the medical syringe includes a tubular syringe barrel, a plunger combined with the syringe barrel and reciprocally movable in the syringe barrel, and a gasket attached to a distal end of the plunger, wherein the gasket is the gasket of the first inventive aspect.

Effects of the Invention

With the provision of the minute groove structure circumferentially extending in the surface of the gasket, according to the present invention, compressive stresses are increased in portions of the gasket adjacent to the groove in the syringe barrel, making it possible to reliably seal an inside liquid drug.

Further, the minute groove structure is formed circumferentially of the gasket after the molding of the gasket. This makes it possible to fill scratches formed perpendicularly to the circumferential direction in the circumferential surface portion of the gasket during the molding of the gasket.

In addition, the depth of the groove is not less than the predetermined percentage of the thickness of the film, thereby improving the slidability of the gasket inserted in the syringe barrel.

According to the present invention, the laminated gasket for the medical syringe is excellent in slidability and sealability. Particularly, the laminated gasket is suitable for a prefilled syringe.

EMBODIMENTS OF THE INVENTION

With reference to the attached drawings, one embodiment of the present invention will hereinafter be described specifically.

Figure 1:
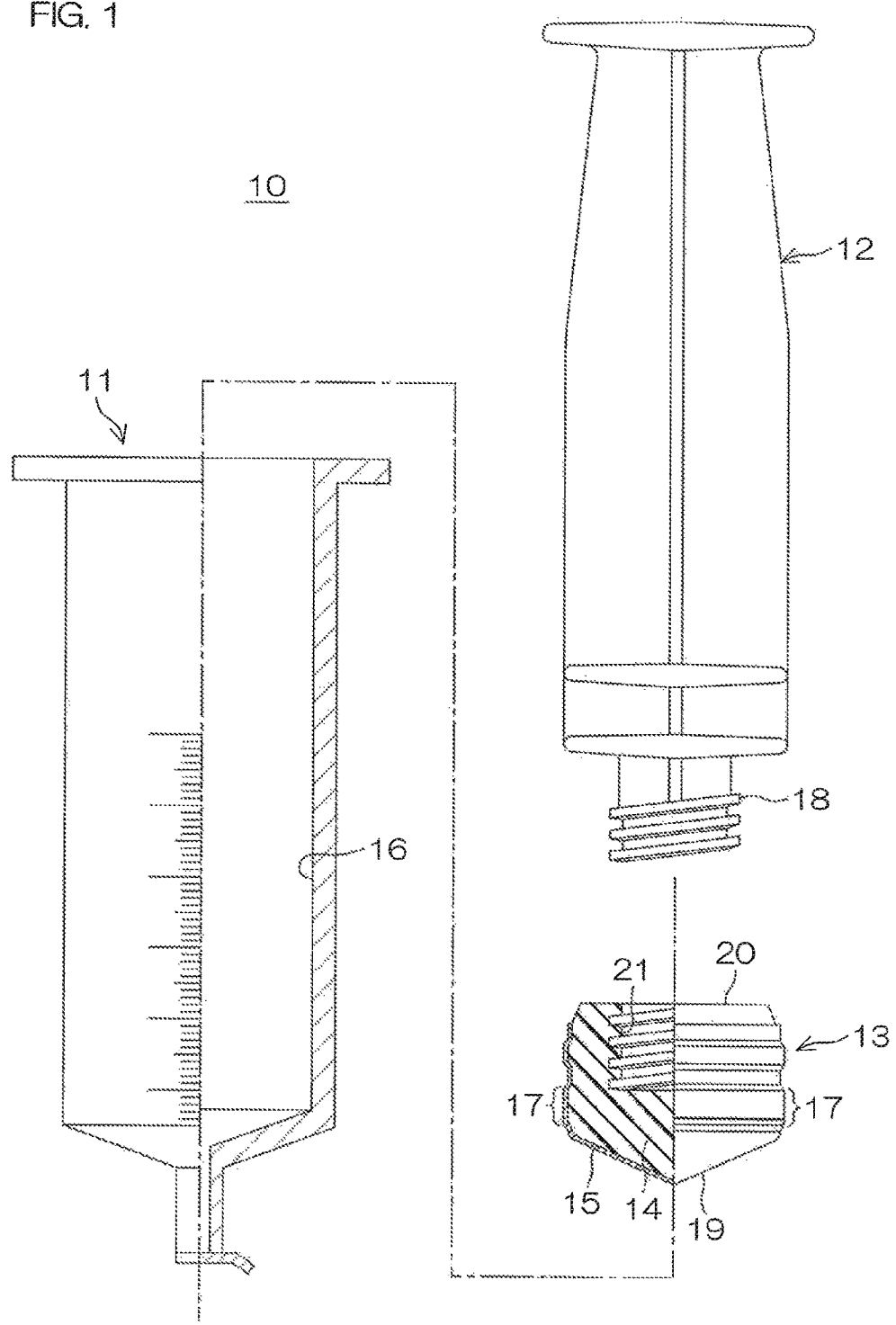
FIG. 1 is a diagram illustrating a medical syringe according to one embodiment of the present invention in an exploded state.

FIG. 1 is a diagram illustrating a medical syringe (so-called prefilled syringe) according to one embodiment of the present invention in an exploded state. In FIG. 1, a syringe barrel 11 and a gasket 13 are shown half in section.

Referring to FIG. 1, the prefilled syringe 10 includes a hollow cylindrical syringe barrel 11, a plunger 12 combined with the syringe barrel 11 and reciprocally movable in the syringe barrel 11, and a gasket 13 attached to a distal end of the plunger 12. The gasket 13 is a so-called laminated gasket which includes a main body 14 made of an elastic material (a rubber, an elastomer or the like), and a lamination film 15 provided on a surface of the main body 14. The gasket 13 has a circumferential surface portion 17 which is kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face, for example, having a conical center portion projecting at an obtuse angle, and a rear end face axially recessed into an engagement recess 21 shaped in a female screw. The head 18 of the plunger 12 is screwed into the engagement recess 21 of the gasket 13, whereby the gasket 13 is attached to the distal end of the plunger 12.

Figure 2:
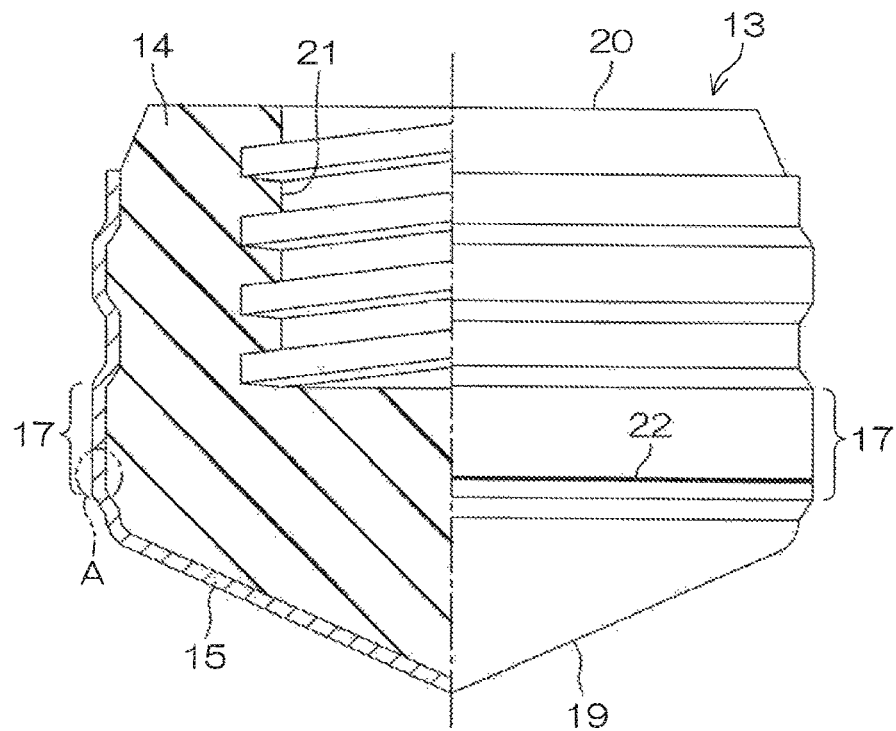
FIG. 2 is a diagram of a laminated gasket according to the embodiment of the present invention with a half of the gasket illustrated in section.

FIG. 2 is a diagram showing only the gasket 13 of FIG. 1 on an enlarged scale with a half of the gasket 13 shown in section.

Referring to FIG. 2, the structure of the gasket 13 according to this embodiment will be described in greater detail.

The gasket 13 includes the main body 14, and the lamination film 15 provided on the surface of the main body 14. The main body 14 is merely required to be made of an elastic material, which is not particularly limited. Examples of the elastic material include thermosetting rubbers and thermoplastic elastomers. Particularly, the thermosetting rubbers and dynamically crosslinkable thermoplastic elastomers having crosslinking sites are more preferred, because they are highly heat-resistant. These polymers are not particularly limited, but preferred examples of the polymers include ethylene-propylene-diene rubbers and butadiene rubbers which are excellent in moldability. Other preferred examples of the polymers include butyl rubbers, chlorinated butyl rubbers and brominated butyl rubbers which are excellent in gas permeation resistance.

The type of the lamination film 15 to be provided on the surface of the main body 14 is not particularly limited, as long as the lamination film is capable of preventing migration of substances from the crosslinked rubber (main body 14) and has more or excellent slidability, i.e., a smaller friction coefficient, than the rubber. Examples of the lamination film include films of ultrahigh molecular weight polyethylenes and fluororesins which are proved to be practical in medical applications. Particularly, the fluororesins are preferred because of their excellent slidability and surface chemical stability. Usable examples of the fluororesins include conventionally known fluorine-containing resins, such as PTFE, modified PTFE, ethylene tetrafluoroethylene copolymers (ETFE) and perfluoroalkyl ether polymers (PFA). The PTFE and the modified PTFE are preferred because of their excellent slidability and chemical stability. The ETFE is preferred because of its resistance to γ-ray sterilization. For adhesiveness to the main body 14, a film made of a mixture of these resins or a laminate film of these resins may be used.

Features of the laminated gasket 13 according to this embodiment are that the gasket 13 includes the circumferential surface portion 17 to be kept in gas-tight and liquid-tight contact with the inner peripheral surface 16 of the syringe barrel 11, and that a groove 22 is formed in the circumferential surface portion 17 as extending circumferentially of the gasket 13. The circumferential direction herein extends in a generally horizontal plane (extends in a horizontal plane perpendicular to the axis of the gasket), and desirably extends at an angle within a range of ±10 degrees with respect to the horizontal plane.

The groove 22 is an annular groove extending along the entire circumference of the circumferential surface portion 17. In this embodiment, a single groove 22 is provided in the circumferential surface portion 17 by way of example.

It is merely necessary to provide at least one groove 22, but a plurality of grooves 22 may be provided to be spaced a predetermined distance from each other axially of the gasket 13. The number of the grooves 22 has no particular upper limit. Further, all the grooves 22 are not necessarily required to be annular, but some of the grooves 22 may be discontinuous. In this case, at least one of the grooves 22 is required to extend along the entire circumference of the circumferential surface portion 17.

The groove 22 is preferably an annular groove extending along the circumference of the circumferential surface portion 17 and having a starting point and an end point coinciding with each other in order to provide a uniform liquid drug sealing effect throughout the circumference of the circumferential surface portion 17. Assuming that the circumferential surface portion 17 of the gasket 13 is developed into a plane, the groove 22 preferably has a generally linear shape.

Figure 3:
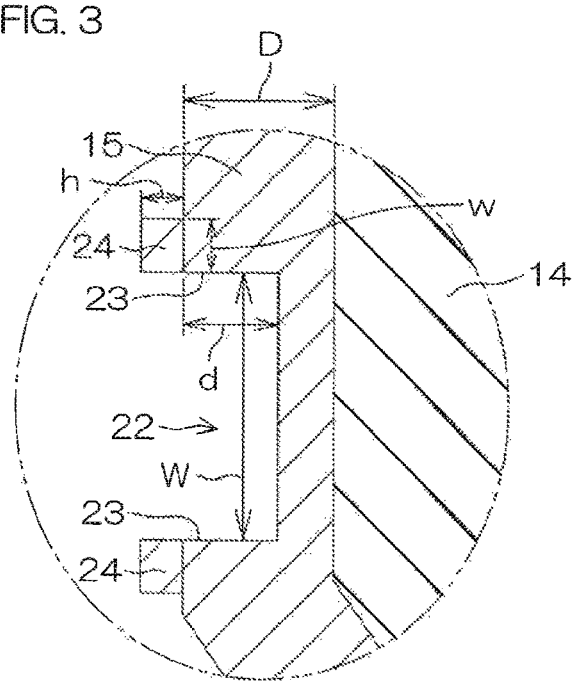
FIG. 3 is an enlarged sectional view of a portion A in FIG. 2.

FIG. 3 is an enlarged partial sectional view of the single groove 22 provided in the circumferential surface portion 17 of FIG. 2, i.e., an enlarged sectional view of a portion A in FIG. 2. Referring to FIG. 3, the groove 22 is recessed into a surface of the lamination film 15.

The thickness D (μm) of a portion of the lamination film 15 present in the circumferential surface portion 17 of the gasket is not particularly limited, but is preferably not less than 10 μm and not greater than 100 μm. If the thickness of the lamination film 15 is excessively great, the gasket 13 is liable to have poorer shape followability when being inserted into the syringe barrel 11, resulting in poorer liquid drug sealability. If the thickness of the lamination film 15 is excessively small, the lamination film 15 is liable to be broken during the molding.

The groove 22 to be formed preferably has a depth d of not less than 0.8D (μm), more preferably not less than D (μm). The depth of the groove 22 has no particular upper limit, but the upper limit is preferably not greater than 1 mm from the viewpoint of the shape stability of the gasket 13.

The width W of the groove 22 to be formed may be properly determined depending upon the depth d of the groove 22 and the physical properties of the lamination film 15 and the rubber of the main body 14, but is preferably not greater than 200 μm, more preferably not greater than 150 μm, further more preferably not greater than 100 μm. An excessively great groove width W is not preferred because, when the gasket 13 is inserted into the syringe barrel 11, the gasket 13 fails to maintain its structure with the bottom of the groove 22 thereof being raised up and pressed against the inner peripheral surface of the syringe barrel 11 due to the elasticity of the compressed rubber (of the main body 14). On the other hand, a groove width W of 1 μm or less is not preferred, because the groove 22 cannot be uniformly formed due to the processing accuracy, failing to provide the intended effects.

The sectional shape of the groove 22 to be formed is not particularly limited. For productivity, the groove 22 preferably has a simply recessed sectional shape or a rounded recessed sectional shape.

The lamination film 15 generally has projections 24 respectively formed along outer edges 23 of the groove 22 as each having a thickness slightly greater than the original thickness D thereof.

Where the surface of the lamination film 15 is cut by means of a cutting blade to form the groove 22, for example, the material (the material of the surface portion of the lamination film 15) is partly compressed into so-called burrs along the outer edges 23 of the groove 22 by the stress to form the projections 24. Where the groove 22 is formed by the laser beam processing, the surface portion of the lamination film 15 is evaporated or decomposed by the laser beam, and the material is partly re-deposited along the outer edges 23 of the groove 22 to form the projections 24.

When the laminated gasket 13 is molded with the use of a mold and then demolded from the mold, the laminated gasket 13 is rubbed against the mold and, therefore, minute scratches are formed on the surface of the laminated gasket 13. Since the groove 22 is formed in the circumferential surface portion of the demolded laminated gasket 13, the projections 24 present along the outer edges 23 of the groove 22 are rather advantageous for filling the minute scratches.

The projections 24 each have any shape without particular limitation, but preferably each have a height h of not less than 2 μm and not greater than 30 μm, more preferably not less than 4 μm and not greater than 25 μm, further more preferably not less than 6 μm and not greater than 23 μm. The projections 24 preferably each have a width w of not less than 2 μm and not greater than 40 μm, more preferably not less than 4 μm and not greater than 35 μm, further more preferably not less than 6 μm and not greater than 30 μm.

Next, a method for producing the gasket 13 according to this embodiment will be described.

The gasket 13 according to this embodiment is produced through the following production process steps:

(1) preparing a gasket molding mold;
(2) molding a gasket having a surface laminated with a lamination film in the mold; and
(3) demolding the laminated gasket from the mold, and then forming a groove in a surface of the gasket circumferentially of a circumferential surface portion of the gasket.

In the step of molding the gasket having the surface laminated with the lamination film in the mold, an unvulcanized rubber is placed on an inner surface of the lamination film in the mold, and vulcanization-molded.

For example, a sheet of an unvulcanized rubber containing a crosslinking agent is stacked on a lamination film 15, and vulcanization-molded in the mold. Thus, the gasket is produced as having a predetermined shape.

In this case, the inner surface of the lamination film 15 on which the rubber sheet is stacked is preferably preliminarily roughened. With the inner surface of the film 15 roughened, the rubber can firmly adhere to the film 15 by the vulcanization molding without the use of an adhesive agent or the like. The adhesion is attributable to an anchoring effect which is created with the vulcanized rubber intruding into voids formed in the roughened inner surface of the film 15.

The modification of the inner surface of the lamination film 15 for the roughening may be achieved, for example, by applying ion beam to the inner surface to break the internal molecular structure in the inner surface (see, for example, JP4908617).

Another production method may be employed which includes the steps of applying an adhesive layer on an inner surface of a lamination film 15 not roughened, superposing an unvulcanized rubber material on the adhesive layer, and putting the lamination film and the rubber material in a mold to mold a gasket in the mold.

After the molding of the gasket in the mold, the groove is formed in a circumferential surface portion of the gasket. Thus, the gasket is produced as having excellent sealability.

In a production method in which the molding of the gasket and the formation of the groove are simultaneously achieved, i.e., in a production method in which a groove structure is preliminarily formed in the mold and is transferred onto the surface of the gasket, the molded gasket is liable to be minutely scratched or damaged when being taken out of the mold (demolded).

Where the groove is formed after the molding of the gasket, in contrast, the scratches formed during the demolding of the gasket can be repaired to some extent in the subsequent groove forming step. Further, the groove formed after the molding of the gasket advantageously provides the intended effects.

Conceivable methods for forming the groove after the molding of the gasket are:

(1) a plastic deformation method in which the gasket including the main body and the lamination film provided on the surface of the main body is plastically deformed by application of an external stress; and (2) a cutting method in which a surface layer of the gasket is cut to be formed with the groove.

Of these methods, the latter cutting method is more preferred, because the groove can be more easily formed by the cutting method than by the plastic deformation method and the stress is less liable to influence the other portion of the lamination film not formed with the groove.

The cutting may be achieved with the use of a cutting blade or by irradiation with a laser beam not by way of limitation. The cutting by the irradiation with the laser beam is more preferred, because the minute groove structure can be easily formed and the stress is less liable to influence a portion of the lamination film around the groove formation portion.

Where the cutting is achieved by the irradiation with the laser beam, the type and the output of the laser beam to be used may be determined in conformity with a conventional technique. The type of the laser beam may be properly selected according to the film material and the depth of the groove. An infrared laser beam is preferably used for the cutting because of its industrially easy handling. The period for the irradiation with the laser beam may be properly selected according to the cutting conditions. Particularly, irradiation with a short-pulse laser beam is preferred with little thermal influence on the portion of the film around the groove formation portion.

EXAMPLES

Two types of lamination films were each used in combination with an unvulcanized rubber, and gaskets were produced by vulcanization molding of the rubber. Gasket products (Examples 1 to 5 and Comparative Examples 2 to 4) were each produced by forming a circumferential annular groove in a circumferential surface portion of the gasket, and a gasket product (Comparative Example 1) was produced without forming a circumferential groove.

The following two types of lamination films were prepared.

[Lamination Films]
(1) PTFE film (VALFLON (registered trade name) available from Nippon Valqua Industries Ltd.)

(2) Modified PTFE film (VALFLON Exl (registered trade name) available from Nippon Valqua Industries Ltd.)

An inner surface of each of the lamination films (on which a sheet of the unvulcanized rubber was stacked) was preliminarily irradiated with ion beam to be thereby roughened.

[Materials for Main Body]
Unvulcanized rubber sheet: Halogenated butyl rubber
Crosslinking agent: 2-di-n-butylandno-4,6-dimercapto-s-triazine available under the registered trade name of ZISNET DB from Sankyo Kasei Co., Ltd.

[Conditions for Production]
Vulcanization temperature: 180° C.
Vulcanization period: 8 minutes
Processing pressure: 20 MPa

[Product Shape]
Gaskets were each molded as having a shape shown in FIG. 2 with a circumferential surface portion 17 thereof having a diameter of 6.60 mm.

[Formation of Groove]
The formation of the groove was achieved by the following laser beam processing after the gaskets were each molded as having the aforementioned product shape. Apparatus: 3-Axis CO2 Laser Marker ML-Z9550T available from Keyence Corporation.

A laser beam having a wavelength of 9300 nm was applied for the processing.

[Test Method]
Measurement of Dimensions of Groove
By means of a laser microscope (VK-X100 available from. Keyence Corporation), the surface geometry of each of the gasket products formed with the groove was measured with an objective lens having a magnification of 50×. For each of the gasket products, the maximum depth and the width of the groove were measured at four positions on an image of the product, and arithmetic averages were determined for the maximum depth and the width.

Liquid Drug Sealability
The gasket products thus each formed with the groove and the gasket product formed without the groove were each inserted into a syringe barrel, which was in turn filled with a test liquid. Then, an opposite end of the syringe barrel was capped. The resulting syringe barrel was allowed to stand still at 40° C. for one week, and then observed with an objective lens having a magnification of 50× by means of a video microscope (DVM5000 available from Leica Microsystems Inc.) to be checked for liquid leakage. For each of the gasket products, 20 samples were observed, and the number of samples suffering from liquid leakage (in which the test liquid penetrated beyond a maximum diameter portion (circumferential surface portion 17) of the gasket product) was recorded. A gasket product with two or less samples suffering from the liquid leakage was rated as acceptable. The test liquid herein used was prepared by adding 0.2 g/liter of a colorant (Methylene Blue available from Sigma Aldrich Japan LLC.) and 1.0 g/liter of a surfactant (POLYSORBATE 80 available from NOF Corporation) to water. The syringe barrel was made of a cycloolefin resin and had an inner diameter of 6.35 mm.

Slidability
The processed gasket products were each inserted into the syringe barrel, and a force required for squeezing the gasket product at a speed of 100 mm/min in the syringe barrel by a plunger was measured by means of a precision universal tester (AG-X 100 kN available from Shimadzu Corporation). An average force required for sliding the gasket product for a sliding distance of 10 mm to 15 mm was determined, and recorded as a sliding resistance.

TABLE 1

| | Example 1 | Example 2 | Example 3 |
|---|---|---|---|
| Film | PTFE | PTFE | Modified PTFE |
| Thickness D (μm) of film | 22.3 | 20.9 | 22.1 |
| Processing method of groove | Laser | Laser | Laser |
| Depth d (μm) of groove | 40.4 | 38.6 | 25 |
| Width (μm) of groove | 100 | 96 | 60 |
| Height (μm) of outer edge portion | 21.6 | 20.8 | 12.5 |
| Width (μm) of outer edge portion | 27.9 | 23.8 | 21.6 |
| Number of grooves | 4 | 1 | 4 |
| Number of samples suffering from liquid leakage | 0 | 0 | 0 |
| Sliding resistance (N) | 9.2 | 9.9 | 9.6 |

| | Example 4 | Example 5 | Comparative Example 1 |
|---|---|---|---|
| Film | Modified PTFE | Modified PTFE | PTFE |
| Thickness D (μm) of film | 19.6 | 38.6 | 20.4 |
| Processing method of groove | Laser | Laser | (no groove) |
| Depth d (μm) of groove | 18 | 52.6 | — |
| Width (μm) of groove | 55 | 113 | — |
| Height (μm) of outer edge portion | 10.8 | 22.5 | — |
| Width (μm) of outer edge portion | 20.9 | 28.4 | — |
| Number of grooves | 4 | 4 | — |
| Number of samples suffering from liquid leakage | 0 | 0 | 13 |
| Sliding resistance (N) | 10.3 | 9.8 | 15 |

| | Comparative Example 2 | Comparative Example 3 | Comparative Example 4 |
|---|---|---|---|
| Film | PTFE | PTFE | Modified PTFE |
| Thickness D (μm) of film | 21.7 | 20.3 | 22.6 |
| Processing method of groove | Laser | Laser | Laser |
| Depth d (μm) of groove | 8.1 | 7.4 | 10.3 |
| Width (μm) of groove | 50 | 55 | 70 |
| Height (μm) of outer edge portion | 5.6 | 5.1 | 8.1 |
| Width (μm) of outer edge portion | 14.6 | 12.3 | 15.1 |
| Number of grooves | 4 | 1 | 4 |
| Number of samples suffering from liquid leakage | 1 | 2 | 0 |
| Sliding resistance (N) | 12.7 | 13 | 12.3 |

[Test Results]

The gasket products of Examples 1 to 5 were each more excellent with a smaller number of samples suffering from the liquid leakage and a lower sliding resistance than the gasket product of Comparative Example 1 not formed with the groove after the molding. The gasket products of Examples 1 to 5 were each more excellent with a lower sliding resistance than the gasket products of Comparative Examples 2 to 4.

This application corresponds to Japanese Patent Application No. 2015-145697 filed in the Japan Patent Office on Jul. 23, 2015, the disclosure of which is incorporated herein by reference in its entirety.

What is claimed is:

1. A gasket for use in a medical syringe, the gasket comprising:
    a main body made of an elastic material; and
    a lamination film provided on a surface of the main body;
    wherein the gasket has a circumferential surface portion to be kept in contact with an inner peripheral surface of a syringe barrel of the syringe,
    wherein the circumferential surface portion is covered with the lamination film;
    wherein the lamination film has at least one cut groove recessed into the lamination film which extends circumferentially from a surface portion of the film; and
    wherein the cut groove has a depth of not less than 0.8D (μm) wherein D (μm) is a thickness of the lamination film present in the circumferential surface portion of the gasket.

2. The gasket according to claim 1, wherein the depth of the cut groove is not less than D (μm).

3. The gasket according to claim 1, wherein the cut groove is a groove formed by laser processing.

4. A gasket production method for producing the gasket of claim 1 for use in a medical syringe, the method comprising the steps of:
    preparing a gasket molding mold;
    molding a gasket in the mold, the gasket having a surface laminated with a lamination film and including a circumferential surface portion covered with the lamination film;
    removing the gasket from the mold; and
    forming a cut groove recessed into the lamination film which extends circumferentially from a surface portion of the film taken out from the mold,
    wherein the forming of the cut groove includes digging and recessing into the surface portion of the lamination film.

5. The gasket production method according to claim 4, wherein the circumferential cut groove is formed in the circumferential surface portion of the gasket by laser irradiation in the cut groove forming step.

6. A medical syringe comprising:
    a tubular syringe barrel;
    a plunger combined with the syringe barrel and reciprocally movable in the syringe barrel; and
    a gasket attached to a distal end of the plunger;
    wherein the gasket is the gasket according to claim 1.

* * * * *